(12) United States Patent
Abidi et al.

(10) Patent No.: US 8,647,391 B2
(45) Date of Patent: Feb. 11, 2014

(54) MALLEOLAR REPLACEMENT DEVICES

(75) Inventors: Nicholas A. Abidi, Scotts Valley, CA (US); Jonathan Borkowski, Scotts Valley, CA (US)

(73) Assignee: Global Orthopaedic Solutions LLC, Scotts Valley, CA (US)

( * ) Notice: Subject to any disclaimer, the term of this patent is extended or adjusted under 35 U.S.C. 154(b) by 0 days.

(21) Appl. No.: 13/178,208

(22) Filed: Jul. 7, 2011

(65) Prior Publication Data

US 2012/0185057 A1 Jul. 19, 2012

Related U.S. Application Data

(60) Provisional application No. 61/362,122, filed on Jul. 7, 2010.

(51) Int. Cl.
*A61F 2/42* (2006.01)

(52) U.S. Cl.
USPC ........................................ 623/21.18; 128/898

(58) Field of Classification Search
USPC ........................................ 623/21.18; 128/898
See application file for complete search history.

(56) References Cited

U.S. PATENT DOCUMENTS

| 3,709,218 | A | 1/1973 | Halloran |
| 5,248,313 | A | 9/1993 | Greene et al. |
| 6,488,712 | B1 | 12/2002 | Tornier et al. |
| 2005/0070902 | A1 | 3/2005 | Medoff |
| 2007/0112432 | A1 | 5/2007 | Reiley |
| 2007/0173947 | A1* | 7/2007 | Ratron et al. ............... 623/21.18 |
| 2009/0105840 | A1* | 4/2009 | Reiley ......................... 623/21.18 |

OTHER PUBLICATIONS

International Search Report and Written Opinion dated Nov. 16, 2011 in International Patent Application Serial No. PCT/US 11/43207.
International Preliminary Report on Patentability for PCT/US11/43207, dated Aug. 1, 2012.

* cited by examiner

*Primary Examiner* — David Isabella
*Assistant Examiner* — Ann Schillinger
(74) *Attorney, Agent, or Firm* — Ryan Kromholz & Manion, S.C.

(57) ABSTRACT

A prosthesis and kit for replacing an ankle joint, and methods of applying the devices or systems. The prosthesis is an intramedullary device directed towards replacement of either of the tibia or fibula bone, wherein the prosthesis is a replacement for the lateral malleolus or the medial malleolus, respectively.

8 Claims, 10 Drawing Sheets

MALLEOLAR REPLACEMENT DEVICES

RELATED APPLICATIONS

The present application claims the benefit of U.S. Provisional Application Ser. No. 61/362,122, filed on 7 Jul. 2010.

BACKGROUND OF THE INVENTION

The invention relates to ankle replacement prostheses and systems, as well as associated surgical instruments and procedures. The present invention is more specifically towards intramedullary ankle joint replacements.

Until the early to mid 1970's, patients with injured or diseased ankle joints commonly resulting from rheumatism, or degenerative or traumatic arthritis, had few options when their ankle joints failed. The most common procedure to help these patients regain some use of their ankle was obliteration of the joint by fusion, a procedure that is still commonly used today. Fusion, however, rendered the ankle stiff and generally immobile relative to the lower leg, resulting in limited use and additional stresses on the knee and hip joints.

Probably the first reported use of total ankle prosthesis was by Buckholz in 1969. The medical community recognized that such ankle replacement led to largely increased use of the ankle joint because the replacement permitted ankle ranges of motion which generally attempted to mimic the natural human joint. Since that time, ankle replacement prostheses have become increasingly common in use and improved in design.

Ankle fractures are particularly common in people having bone disease, such as osteoporosis. Geriatrics, particularly woman, are very susceptible to ankle fractures, and the prognosis after fracture is generally poor, even with the use of a prosthesis. In general, currently used prostheses do not afford the necessary flexibility required for an ankle joint and recovery can be slow and arduous. The fusing together of bones or bone segments required and carried out with prior prostheses limits the ability of the ankle joint to completely heal properly, particularly with those who may have limited mobility prior to the ankle fracture.

Stability and weight bearing are other issues that are more important when replacing an ankle joint as opposed to other joints. For example, hip, shoulder, or knee joints are not required to bear the load that is required from an ankle joint. Consequently the use of replacement devices for these other joints does not necessarily translate to possible joints for an ankle joint.

SUMMARY OF THE INVENTION

The present invention is directed towards a prosthesis and kit for replacing an ankle joint, and methods of applying the devices or systems. The prosthesis is an intramedullary device directed towards replacement of either of the tibia or fibula bone, wherein the prosthesis is a replacement for the lateral malleolus or the medial malleolus, respectively.

The device has a first end that is inserted into the intramedullary canal of either the fibula or tibia. A second end of the device is shaped and configured to assimilate the shape of the lateral or medial malleolus, respectively. The device will be secured to the respective tibia or fibula. Likewise, a system could comprise two devices, wherein one is directed towards each of the tibia and fibula.

The invention also contemplates methods of installing or inserting the device, wherein the particular malleolus is resected, sufficiently or completely so that the device will replicated the contours of the bone once inserted. The first end of the device is inserted into the intramedullary canal and secured to the bone.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
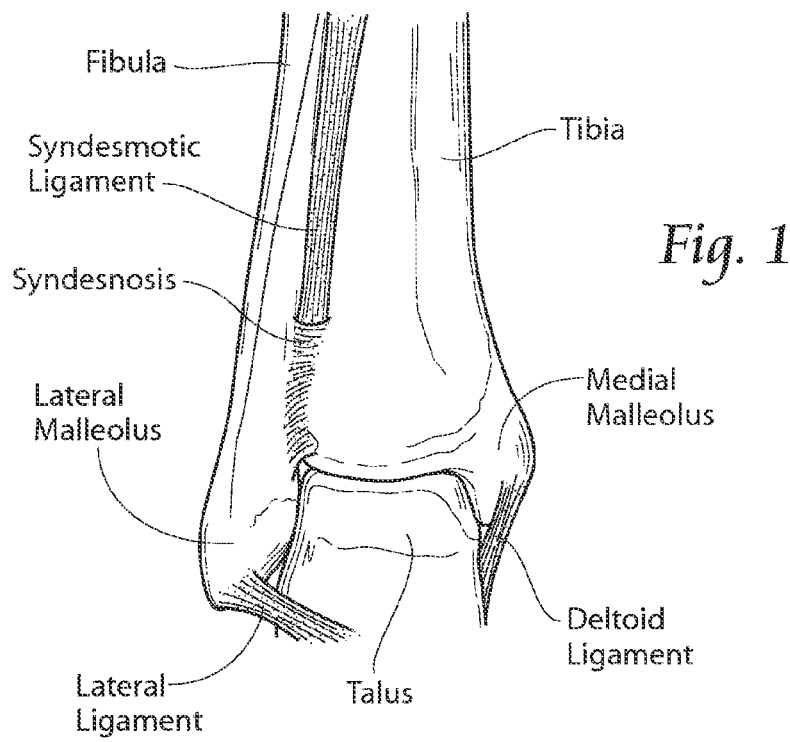
FIG. 1 is a perspective view of an ankle joint.

FIG. 1 depicts a normal ankle joint, free of fracture. The ankle generally consists of the distal ends of the fibula and tibia bones, which are connected to the talus bone. The fibula bone comprises the lateral malleolus, which is connected to the talus by way of the lateral ligament. The tibia bone comprises the medial malleolus, which is connected to the talus by way of the deltoid ligament. The tibia and fibula are connected two one another by way of the syndesmotic ligament.

If undue stress is put on the ankle joint, the joint may fracture, with either the fibula or tibia fracturing, or possibly both. Often a fracture will form at the proximal end of respective malleolus, e.g. the lateral or medial malleolus. Such a fracture of the lateral malleolus is shown in FIG. 2, wherein the fracture is shown on the fibula at the proximal end of the lateral malleolus.

Figure 2:
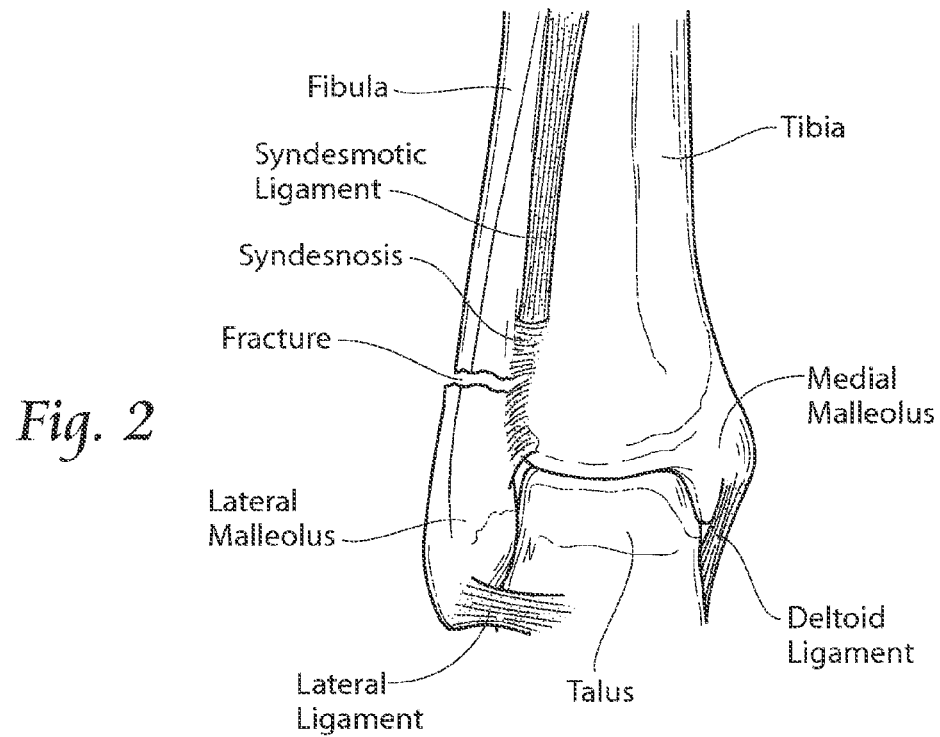
FIG. 2 is a perspective view of the ankle joint of FIG. 1, with a break being shown in the fibula bone.
Figure 3A:
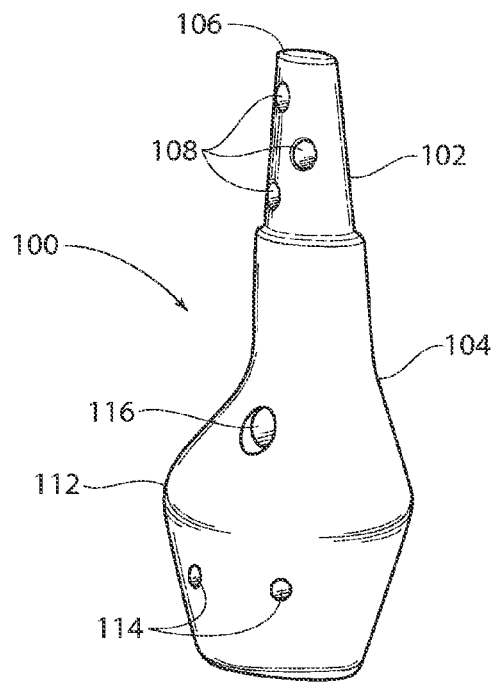
FIG. 3A is a perspective view of an ankle replacement device according to the present invention.
Figure 3B:
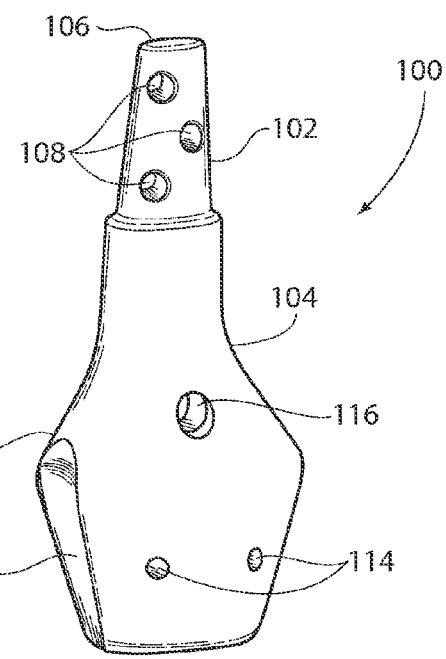
FIG. 3B is a second perspective view of the device of FIG. 3A.
Figure 4:
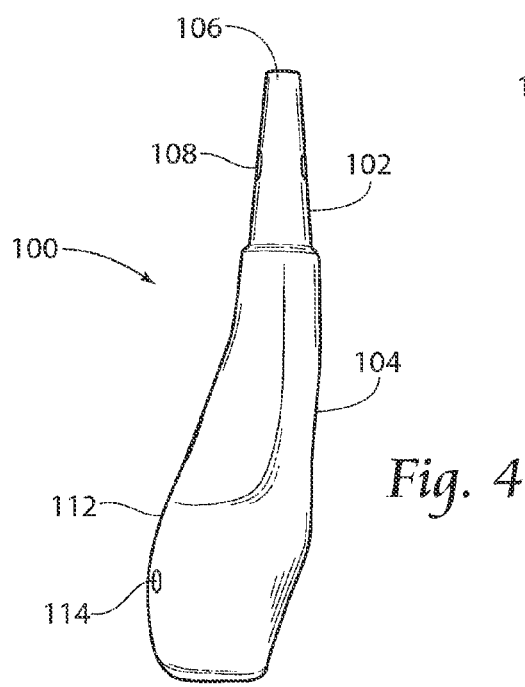
FIG. 4 is a side view of the device of FIG. 3A.

FIGS. 3A-4 depicts a prosthesis 100 according to the present invention to address a fracture as shown in FIG. 2. The prosthesis 100 generally comprises a proximal portion 102 and a distal portion 104. The proximal portion 102 comprises an insert 106 that will be positioned within the intramedullary canal of the fibula. The proximal portion 102 preferably has a smaller diameter than the distal portion 104, so that when the insert 106 is inserted into the intramedullary canal, there is a definite distance that the prosthesis 100 may be inserted into the intramedullary canal. The insert 106 can be of any shape, e.g. a post or wedge or multiple posts or wedges, that will allow the insert 106 to be properly inserted and affixed within the intramedullary canal. The insert 106 has at least one hole 108 and preferably a plurality of holes 108 that will allow screws 110 (see FIG. 7) to attach the prosthesis 100 to the fibula. A plurality of holes 108 is preferable, in that it allows for the insert 106, and the prosthesis 100 in general, to be attached at varying angles and elevations, depending on a particular fracture or on other characteristics, such as the age or gender of the patient.

Still referring to FIGS. 3A-4, the distal portion 104 generally forms a body 112 that is shaped and sized to follow the contours of the lateral malleolus. The body 112 also has an opening 114, and preferably a plurality of openings 114. The openings 114 are generally used during the implantation of the prosthesis as an insertion guide when positioning the prosthesis. The openings 114 may also receive screws 110 so that the distal portion 104 may also be attached to the joint by way of screws 110 (see FIG. 7). As with the insert 106, it is preferable for the body 112 to have a plurality of openings 114 so that the prosthesis 100 can be positioned at varying angles and elevations. A through bore 116 may also be located on the body, which can receive a pin for syndesmotic fixation, if necessary.

The prosthesis 100 is also designed to provide protection for the ankle and surrounding tendons once the prosthesis 100 is inserted. For example, a groove 118 is located in the body 112, which is intended to protect the peroneal tendon once the prosthesis is properly positioned. The peroneal tendon will rest within the groove 118, thereby allowing the groove to act as a shield for the tendon. The body 112 may have a groove 118 on either the right side or the left side of the body 112, or both sides of the body 112, which will allow the prosthesis to be used for a right or left ankle repair.

FIGS. 5-9 depict the prosthesis 100 being secured to the fibula bone. Initially, a doctor, surgeon, or radiologist will take a radiograph or X-ray of the ankle to assist with making a template for the ankle and to assist in properly sizing a prosthesis to be used in the ankle repair.

Figure 5:
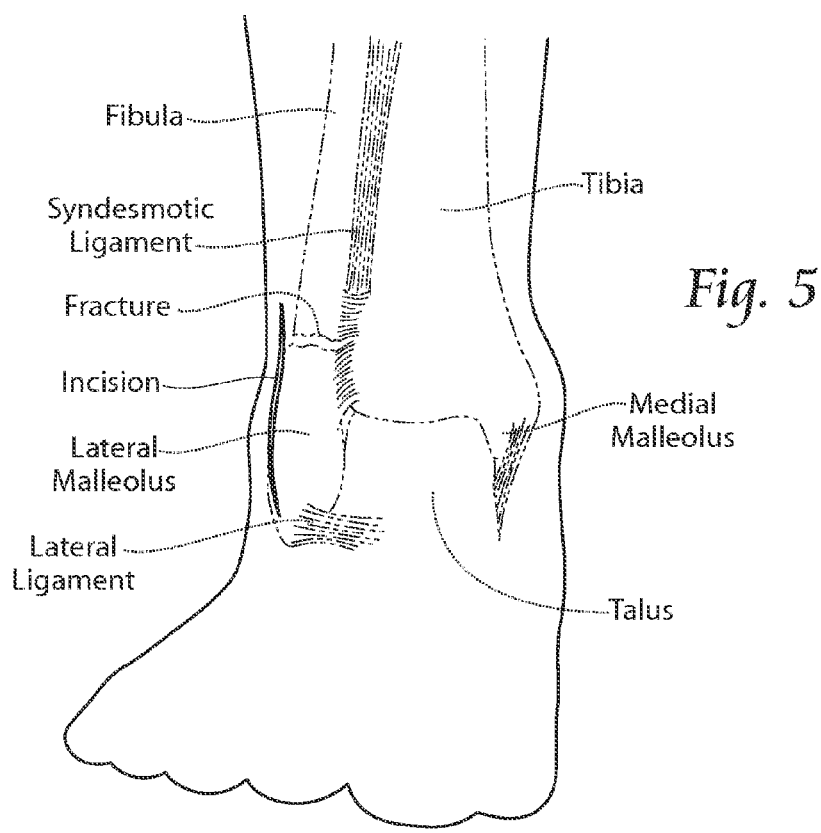
FIG. 5 is a view of the ankle of FIG. 2 showing an incision being made in the skin for eventual insertion of a prosthesis as shown in FIG. 3A.

FIG. 5 shows a doctor or surgeon preparing the fractured ankle of FIG. 2 for insertion of the prosthesis 100. An incision over the lateral malleolus will be cut into the skin of the ankle to thereby expose the malleolus. The tendons, e.g. the peroneal tendon, will be mobilized by the surgeon.

Figure 6:
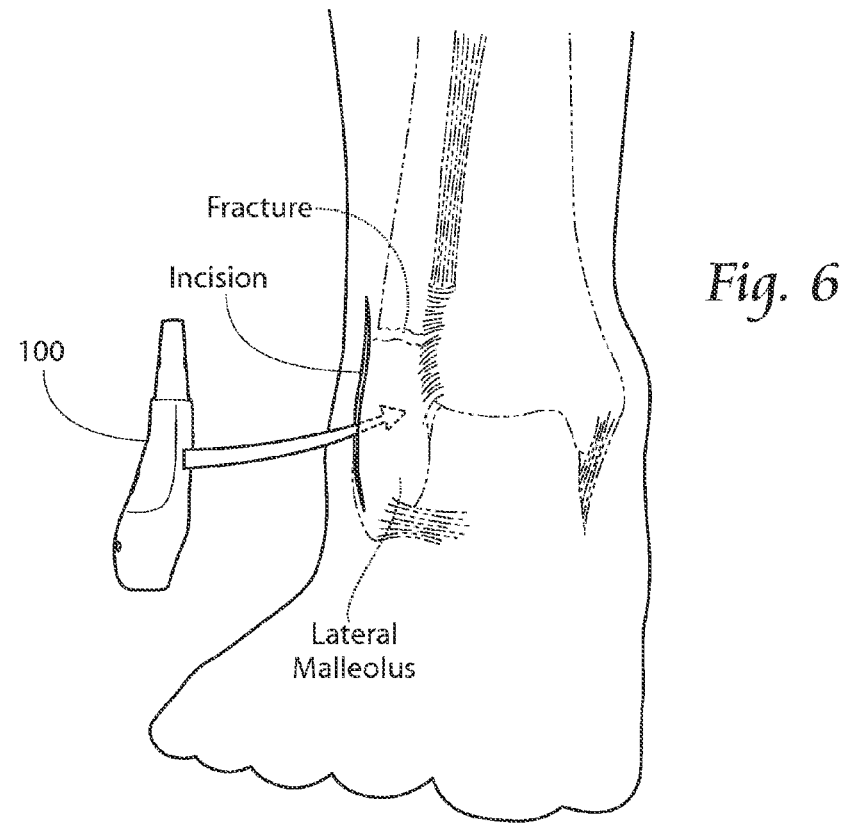
FIG. 6 demonstrates a prosthesis being inserted into the incision of FIG. 5 to determine a properly sized prosthesis.

FIG. 6 show a prosthesis 100 being inserted into the incision. The prosthesis 100 is used as a trial implant to determine the appropriate size for a prosthesis 100 that will eventually be inserted into the incision. The use of a trial implant will also assist in determining the necessary level of bone resection that will be required for the fractured/comminuted bone.

Figure 7:
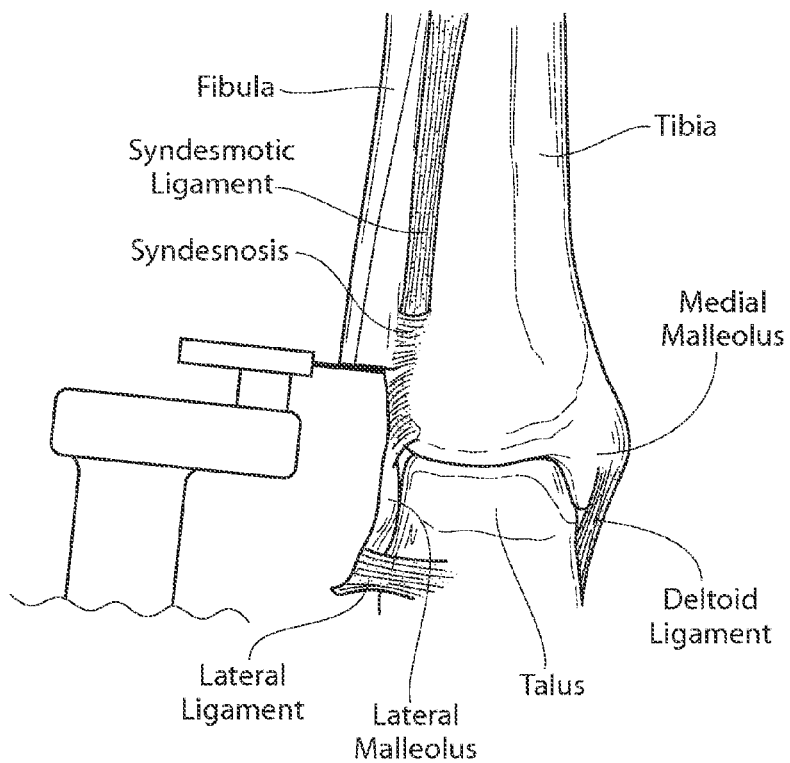
FIG. 7 demonstrates the ankle of FIG. 2 being resected to prepare the ankle for placement of the device of FIG. 3A within the ankle.

FIG. 7 demonstrates the bone being resected for insertion of the prosthesis 100. An oscillating saw is used to cut the bone at the levels of the trial implant (see FIG. 6). The bone is resected so that once the prosthesis 100 is positioned, it will follow the contours of the native lateral malleolus. Similarly, the intramedullary canal will be resected so that it will be shaped to receive the proximal portion 102 of the prosthesis. The resected bone fragments will detached from the ligamentous and tendon attachments so that the properly sized and configured cavity will remain within the ankle joint. The relevant canal, e.g. the endosteal canal, will be enlarged with reamers on the lateral malleolus to insure proper alignment within the cavity. The amount of bone material that will be resected will depend on the size and severity of the fracture.

Figure 8:
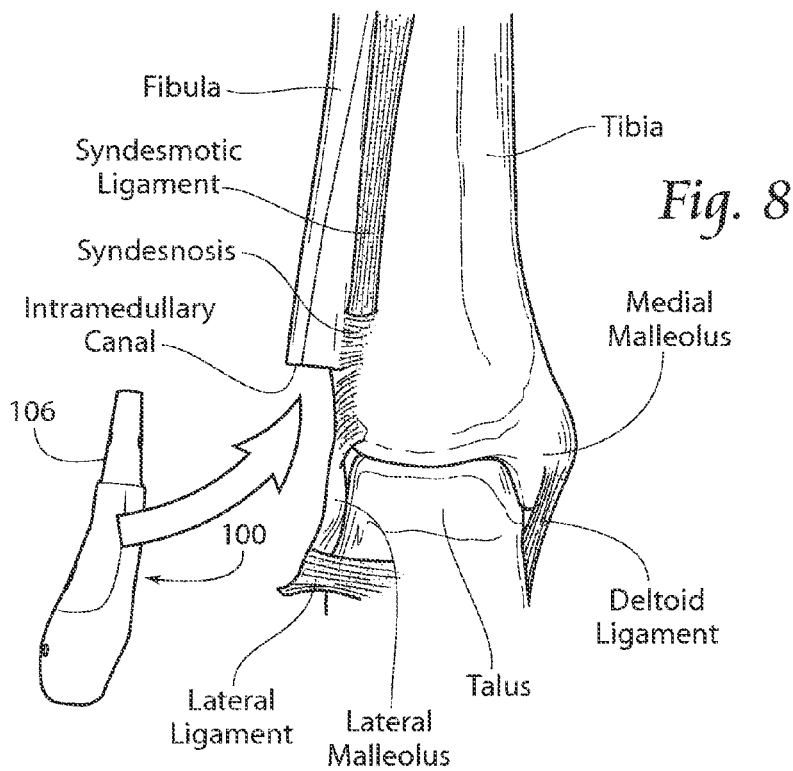
FIG. 8 depict the device of FIG. 3A being inserted into the fibula.

FIG. 8 shows the proximal portion 102 of the prosthesis 100 being inserted into the intramedullary canal so that it may be affixed to the fibula. The prosthesis 100 will be inserted so that it is properly affixed to the fibula, but also to protect the peroneal tendon with the use of the posterior groove 118 The tendon will sit within the groove 118, thereby allowing the groove 118 to protect the tendon. Similarly, as shown in FIG. 8, enough of the lateral malleolus remains around the prosthesis 100 so that the prosthesis 100 is retained properly, which will prevent the prosthesis from unnecessarily moving from side to side once positioned in the ankle.

Figure 9:
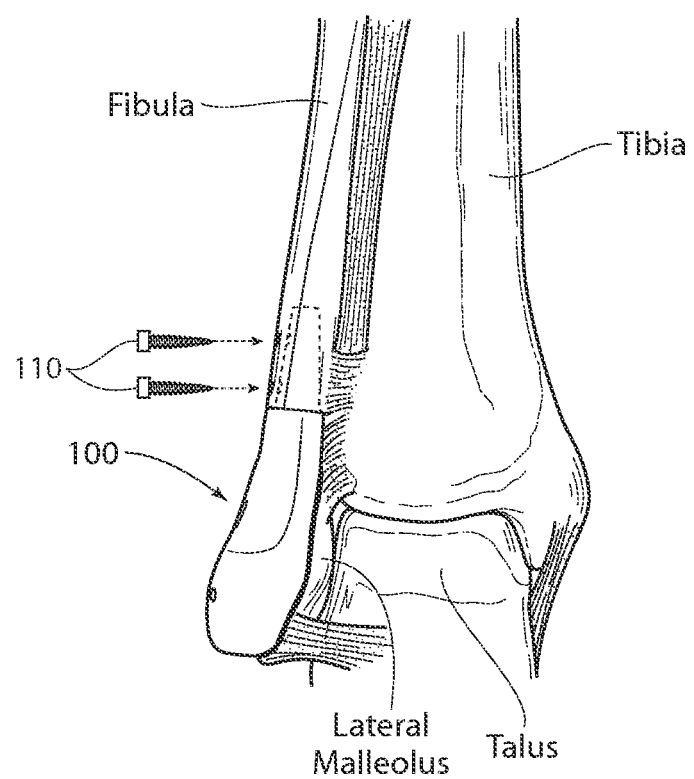
FIG. 9 depicts the device of FIG. 3A being affixed to the ankle.

Once properly inserted, the prosthesis will mimic the shape and contour of the fibula, particularly the lateral malleolus, as shown in FIG. 9. The prosthesis 100 than can be secured to the ankle joint using screws 110. Preferably, the prosthesis 100 is locked in place by securing one or more, e.g. two, screws 110 laterally through fibula, the syndesmosis, and locking the screws to the tibia. Alignment guides may be used to assist insertion of the screws. Screws 110 will also be used to secure the distal portion 104 properly within the lateral malleolus. The resultant arrangement allows for a repaired ankle that will closely resemble the fibula bone prior to fracture, thereby decreasing the amount of time needed for recovery and increasing the chance that the patient will recover mobility and stability of the ankle.

Figure 10:
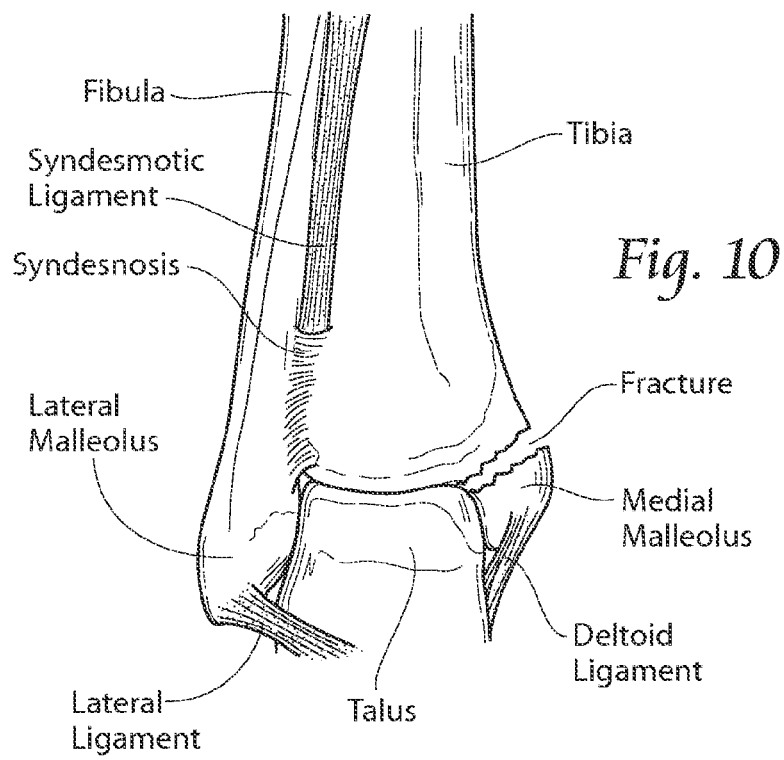
FIG. 10 is a perspective view of the ankle of FIG. 1, with a break being shown in the tibia bone.
Figure 11A:
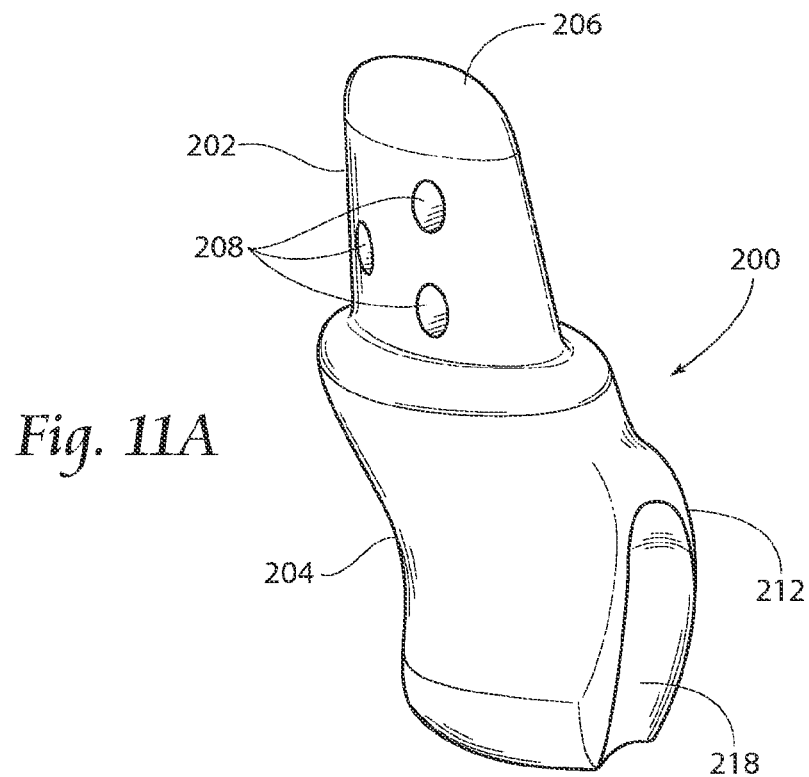
FIG. 11A is a perspective view of a second ankle replacement device according to the present invention.
Figure 11B:
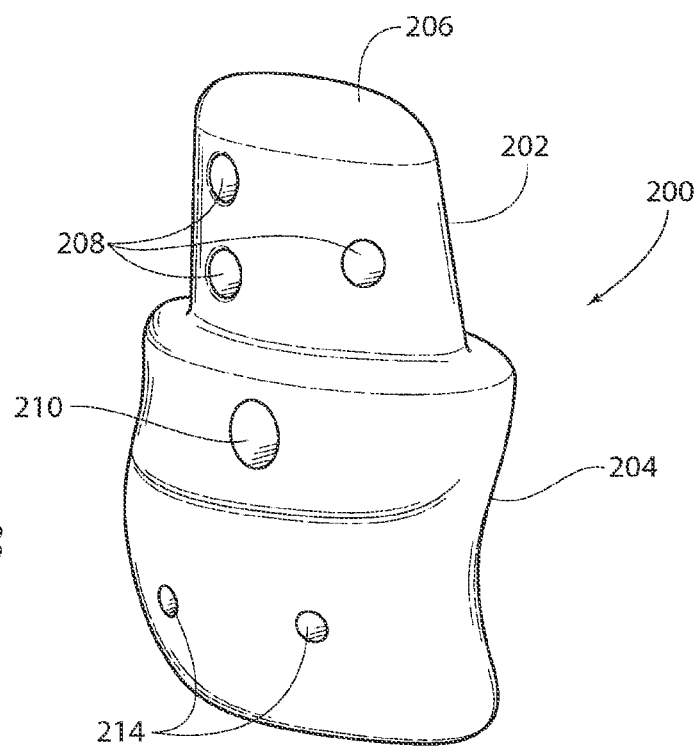
FIG. 11B is second perspective view of the device of FIG. 11A.
Figure 12:
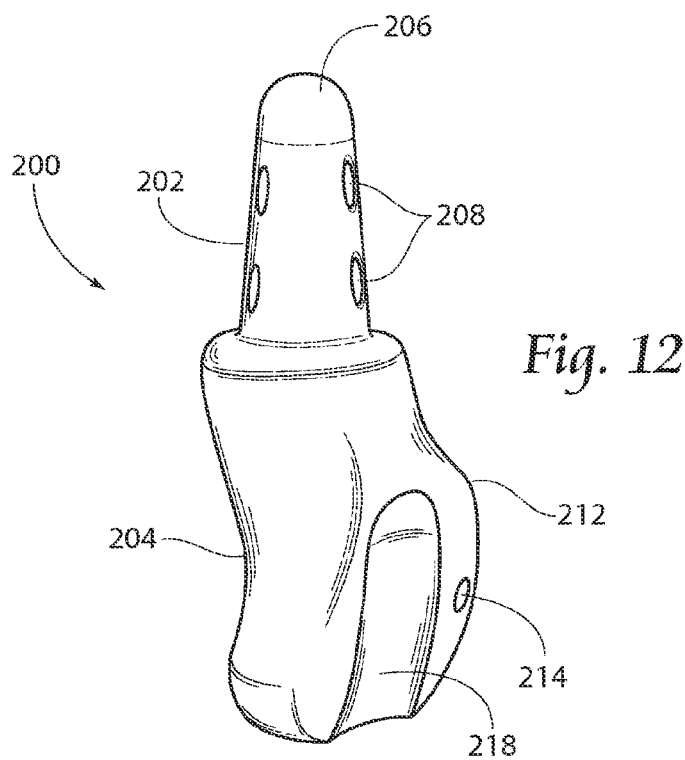
FIG. 12 is a side view of the device of FIG. 11A.

As noted above, a fracture may also occur in the tibia, as opposed to the fibula. Such a fracture is depicted in FIG. 10. Such a fracture typically happens at the proximal end of the medial malleolus. FIGS. 11A-12 show a prosthesis 200 according to the present invention for addressing fractures as shown in FIG. 10. The prosthesis 200 is similar to the prosthesis 100 described above in FIG. 3A-4, except that the prosthesis 200 is directed towards a fracture of the tibia as opposed to the fibula. That is, the prosthesis 200 is designed to be shaped according to the contours of the medial malleolus as opposed to the lateral malleolus.

Still referring to FIGS. 11A-12, the prosthesis comprises a proximal portion 202 and a distal portion 204. The proximal portion comprises an insert 206 that will be inserted into the intramedullary canal of the tibia. As with the prosthesis 100, the proximal portion 202 preferably has a smaller diameter than the distal portion 204, so that when the insert 206 is inserted into the intramedullary canal, there is a definite distance that the prosthesis 200 may be inserted into the intramedullary canal. The insert 206 can be of any shape, e.g. a post or wedge or multiple posts or wedges, that will allow the insert 206 to be properly inserted and affixed within the intramedullary canal. The insert 206 has a hole 208 or plurality of holes 208 for attachment to the tibia by way of screws 210 (see FIG. 13). A plurality of holes 208 is preferable, in that it allows for the insert 206, and the prosthesis 200 in general, to be attached at varying angles and elevations, depending on a particular fracture or on other characteristics, such as the age or gender of the patient.

Still referring to FIGS. 9A-10, the distal portion 204 of the prosthesis 200 generally forms a body 212 that is shaped and sized to follow the contours of the medial malleolus. The body 212 also has an opening 214, and preferably a plurality of openings 214. The openings 214 are generally used during the implantation of the prosthesis as an insertion guide when positioning the prosthesis. The openings 214 may also receive screws 210 so that the distal portion 204 of the prosthesis 200 may also be attached to the ankle joint by way of screws 210 (see FIG. 7). As with the insert 206, it is preferable for the body 212 to have a plurality of openings 214 so that the prosthesis 100 can be positioned at varying angles and elevations. A through bore 216 may also be located on the body, which can receive a pin for syndesmotic fixation, if necessary.

The prosthesis 200 is also designed to provide protection for the ankle and surrounding tendons, e.g. posterior tibial tendon, once the prosthesis 200 is inserted. For example, a groove 218 is located on the body 212, which is intended to protect the posterior tibial tendon once the prosthesis is properly positioned. The posterior tibial tendon will rest within the groove 218, thereby allowing the groove to act as a shield for the tendon. The body 112 may have a groove 218 on either the right side or the left side of the body 212, or both sides of the body 212, which will allow the prosthesis to be used for a right or left ankle repair.

FIGS. 13-17 depict the prosthesis 200 being secured to the tibia bone. Initially, a doctor, surgeon, or radiologist will take a radiograph or X-ray of the ankle to assist with making a template for the ankle and to assist in properly sizing a prosthesis to be used in the ankle repair.

Figure 13:
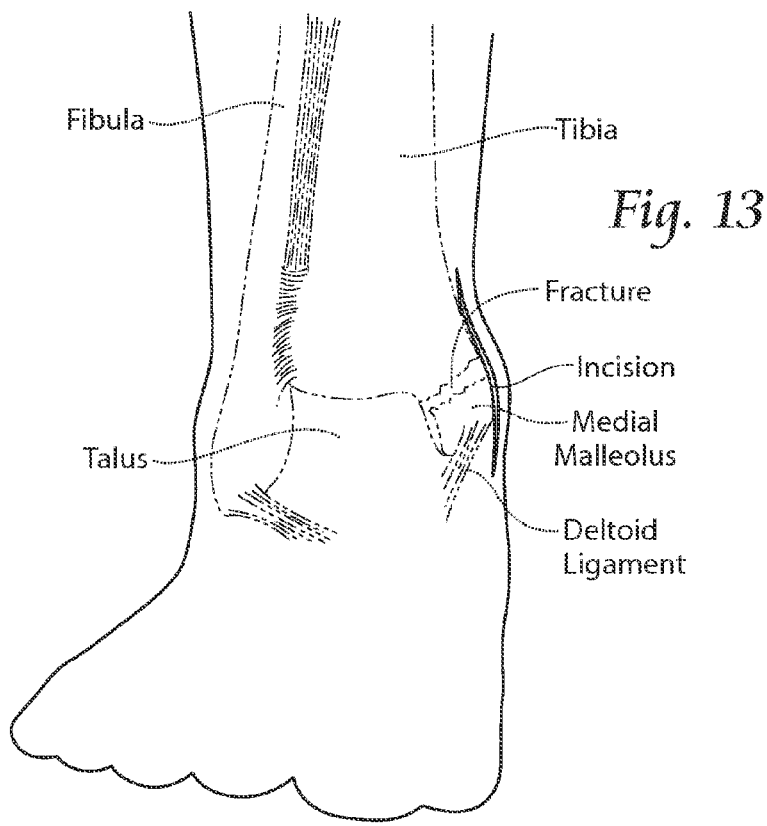
FIG. 13 is a view of the ankle of FIG. 10 showing an incision being made in the skin for eventual insertion of a prosthesis as shown in FIG. 11A.

FIG. 13 shows a doctor or surgeon preparing the fractured ankle of FIG. 10 for insertion of the prosthesis 200. An incision over the lateral malleolus will be cut into the skin of the ankle to thereby expose the malleolus. The tendons, e.g. the posterior tibial tendon, will be mobilized by the surgeon.

Figure 14:
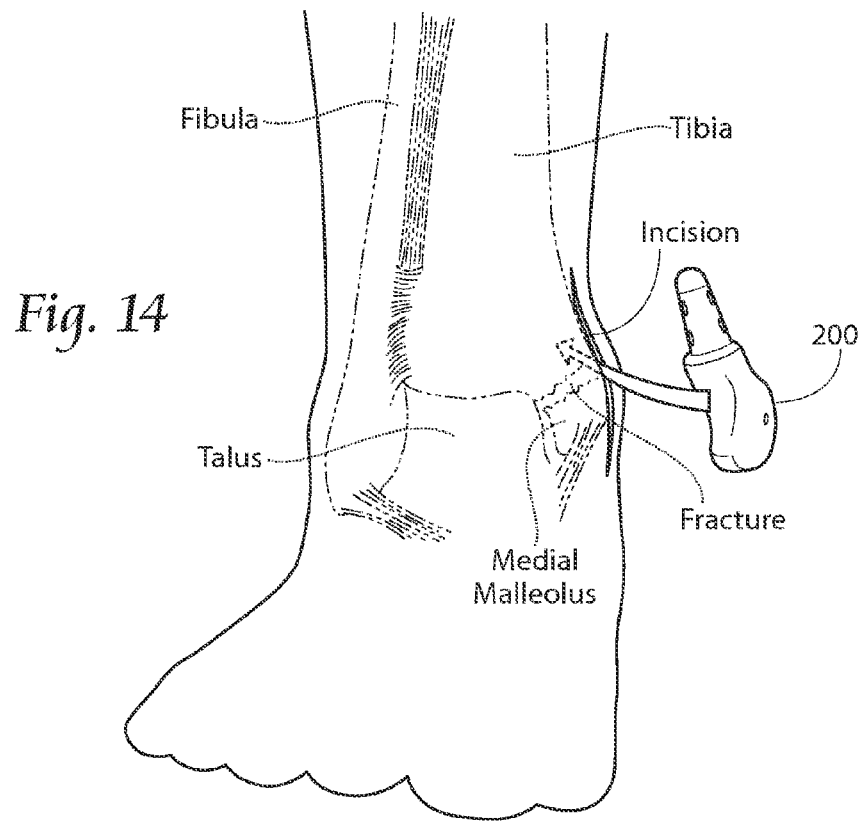
FIG. 14 demonstrates a prosthesis being inserted into the incision of FIG. 13 to determine a properly sized prosthesis.

FIG. 14 show a prosthesis 200 being inserted into the incision. The prosthesis 200 is used as a trial implant to determine the appropriate size for a prosthesis 200 that will eventually be inserted into the incision. The use of a trial implant will also assist in determining the necessary level of bone resection that will be required for the fractured/comminuted bone.

Figure 15:
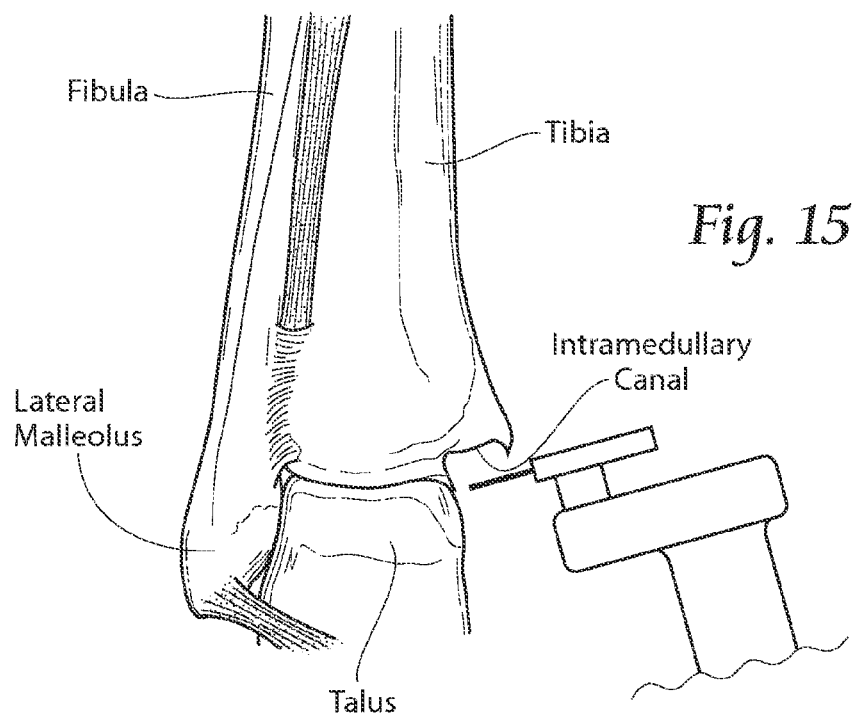
FIG. 15 demonstrates the ankle of FIG. 10 being resected to prepare the ankle for placement of the device of FIG. 11A within the ankle.

Referring to FIG. 15, the tibia bone is resected so that once the prosthesis 200 is positioned within the intramedullary canal, it will follow the contours of the native lateral malleolus. An oscillating saw is used to cut the bone at the levels of the trial implant (see FIG. 14). In the same fashion, the intramedullary canal will be resected so that it will be shaped to properly receive the proximal portion 202 of the prosthesis. The resected bone fragments will detached from the ligamentous and tendon attachments so that the properly sized and configured cavity will remain within the ankle joint. The relevant canal, e.g. the endosteal canal, will be enlarged with reamers on the medial malleolus to insure proper alignment within the cavity. The amount of bone material that will be resected will depend on the size and severity of the fracture.

Figure 16:
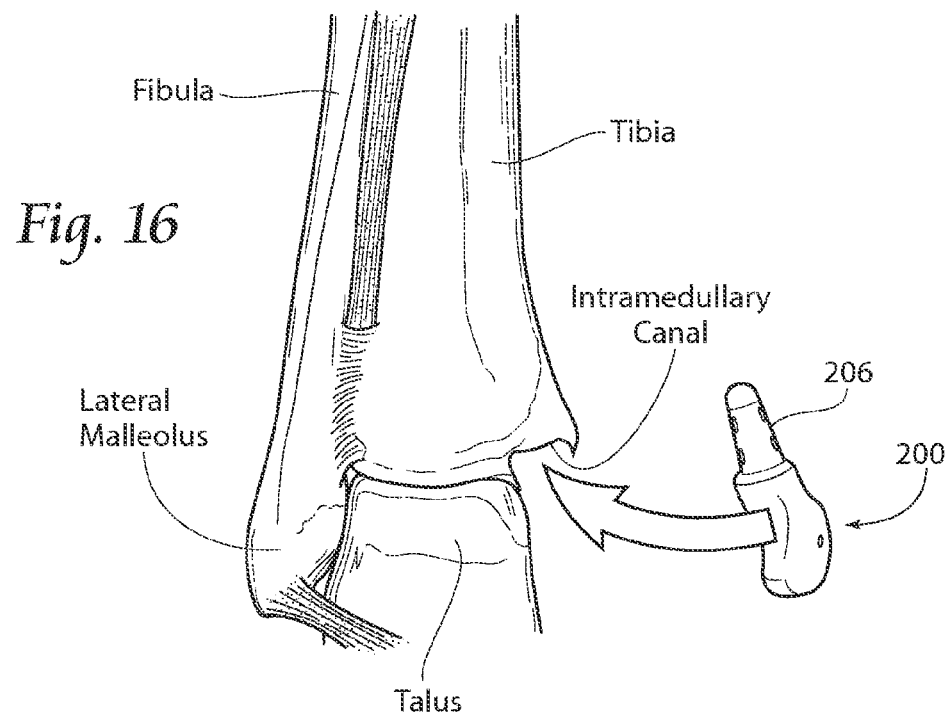
FIG. 16 depicts the device of FIG. 11A being inserted into the ankle.
Figure 17:
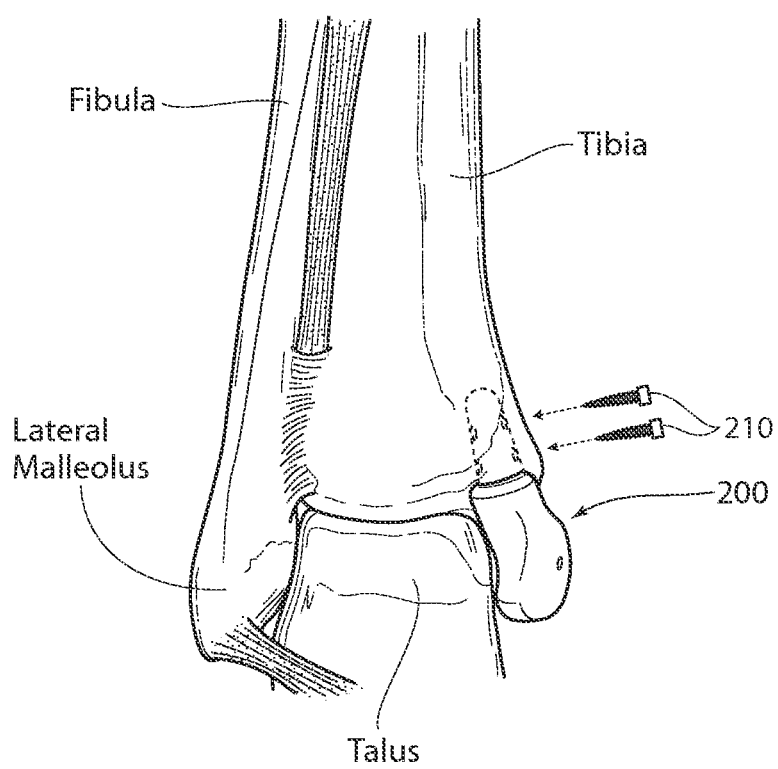
FIG. 17 depicts the device of FIG. 11A being affixed to the ankle.

FIG. 16 shows the proximal portion 202 of the prosthesis 200 being inserted into the intramedullary canal so that it may be affixed to the tibia. Once properly inserted, the prosthesis 200 will mimic the shape and contour of the tibia, particularly the medial malleolus, as shown in FIG. 17. The prosthesis 200 than can be secured to the ankle joint using screws 210. One or more screws 210, e.g. three screws 210, preferably with the screws 210 being in the form of offset screws, will pass through the medial mallelolar cortex, through the intramedullary canal, and ending in the distal side of the tibia, e.g. the tibial metaphysic. The arrangement helps to promote boney in-growth into the prosthesis, thereby increasing the recovery and stability of the repaired ankle. The resultant arrangement allows for a repaired ankle that will closely resemble the fibula bone prior to fracture, thereby decreasing the amount of time needed for recovery and increasing the chance that the patient will recover mobility and stability of the ankle.

The prosthesis 200 will be inserted so that it is properly affixed to the fibula, but also to protect the posterior tibial tendon with the use of the posterior groove 218 (see FIG. 12). The tendon will sit within the groove 218, thereby allowing the groove 218 to protect the tendon and also to prevent the prosthesis from unnecessarily moving from side to side once positioned in the ankle.

As such, the present invention is directed towards a prosthesis generally comprising a proximal portion that will be inserted into the intramedullary canal of a specific bone of the ankle joint, and a distal portion that is shaped and designed to replicate the malleolus section of the particular bone that the prosthesis is used in connection with. By using the prostheses to replicate the shape and form of the bone prior to fracture, these prostheses increase the stability of the ankle joint and also decrease the recovery time, as the ankle joint is capable of bearing weight sooner than prior art devices. Similarly, the intramedullary design also promotes healing and recovery, in that it fosters grafting of the prosthesis to the bone.

The prostheses of the present invention may be made of any suitable biocompatible material. Preferably the prostheses are made of a material that will help with in bone growth. A porous material, e.g. sintered titanium, is one preferred material. For example, the prosthesis 100, 200 may have a titanium porous coating, which assists in bone growth.

It should also be understood that, if necessary, the present invention contemplates a kit that will include both a prosthesis 100 for use with the fibula and a prosthesis 200 for use with the tibia. However, one of the advantages of the present invention over the prior art is that it is not necessary that both the fibula and tibia be resected if one of the bones is not fractured. The prostheses are inserted and attached independently from one another, which also provides for a more efficient reconstruction process for the ankle joint, since alignment of separate prostheses for the fibula and tibia during surgery is not necessary. Likewise, it should be understood that the use of screws 110, 210 refers generally to attachment means for the ankle, e.g. pins, bolts, screws, clamps, etc., that are commonly used in surgical procedures. It is also understood that the length of the screws 210, 110 is determinative on the needs of a particular fracture, including such factors as age of the person requiring the prosthesis. For example, a screw may be sufficiently long so that the screw will intersect syndesmotic ligament, or it may be determined that a shorter screw will be sufficient. Any length of screw 210 or other fastening device will be fall within the scope of the present invention.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A method of repairing an ankle fracture comprising the steps of:
   providing a prosthesis comprising
      a proximal portion shaped for insertion into the intramedullary canal of a lateral malleolus portion of the ankle joint; and a distal portion having an outer surface that is generally shaped and sized to follow the contours of the malleolus portion of the ankle joint, said distal portion further comprising a groove formed in the outer surface for protecting a tendon associated with the bone;

resecting the bone to receive the prosthesis;

inserting the proximal portion of the prosthesis into the intramedullary canal of the bone; and securing the prosthesis to the ankle.

2. The method of claim 1 wherein the bone is the fibula.

3. The method of claim 1 wherein the bone is the tibia.

4. The method of claim 1 further comprising the initial step of using a trial prosthesis to determine the appropriate size of the prosthesis inserted into the bone.

5. The method of claim 1 wherein the distal portion further comprises at least one opening, the method further comprising the steps of providing a fastener, and inserting said fastener through said at least one opening to thereby attach said distal portion to said malleolus.

6. The method of claim 1 wherein the distal portion further comprises a plurality of openings, the method further comprising the steps of providing at least one fastener, determining the proper position of the prosthesis; and securing said fastener through one of said plurality of openings to thereby attach said distal portion to said malleolus at properly determined position.

7. The method of claim 1 wherein the proximal portion further comprises at least one opening, the method further comprising the steps of providing a fastener, and inserting said fastener through said at least one opening to thereby attach said proximal portion within said intramedullary canal.

8. The method of claim 1 wherein the distal portion further comprises a plurality of openings, the method further comprising the steps of providing at least one fastener, determining the proper position of the prosthesis; and securing said fastener through one of said plurality of openings to thereby attach said proximal portion within said intramedullary canal at properly determined position.

* * * * *

UNITED STATES PATENT AND TRADEMARK OFFICE
CERTIFICATE OF CORRECTION

PATENT NO. : 8,647,391 B2
APPLICATION NO. : 13/178208
DATED : February 11, 2014
INVENTOR(S) : Abidi et al.

It is certified that error appears in the above-identified patent and that said Letters Patent is hereby corrected as shown below:

In the Specification

Column 1, line 33, delete "woman" and substitute -- women --

Column 3, line 5, delete "depicts" and substitute -- depict --

Column 4, line 5, after "fragments will" insert -- be --

Column 5, line 31, after "over the" delete "lateral" and substitute -- medial --

Column 5, line 43, after "the native" delete "lateral" and substitute -- medial --

Column 5, line 48, after "fragments will" insert -- be --

Column 6, line 2, delete "fibula" and substitute -- tibia --

Column 6, line 6, after "affixed to the" delete "fibula" and substitute -- tibia --

Column 6, line 50, delete "will be fall" and substitute -- will fall --

Signed and Sealed this
Twenty-ninth Day of April, 2014

Michelle K. Lee
*Deputy Director of the United States Patent and Trademark Office*